United States Patent [19]
Boxall et al.

[11] Patent Number: 5,648,394
[45] Date of Patent: Jul. 15, 1997

[54] TOPICAL COMPOSITION FOR INHIBITING HAIR GROWTH

[76] Inventors: Brian Alfred Boxall, 51 Chatsworth Avenue, Winnersh, Wokingham, Berkshire RG11 5EU, United Kingdom; Geoffrey Wilfred Amery, 183 Church Road, Earley, Reading, Berkshire RG6 1HN, United Kingdom; Gurpreet S. Ahluwalia, 8632 Stableview Ct., Gaithersburg, Md. 20882

[21] Appl. No.: 513,980

[22] PCT Filed: May 27, 1993

[86] PCT No.: PCT/US93/05068

§ 371 Date: Sep. 14, 1995

§ 102(e) Date: Sep. 14, 1995

[87] PCT Pub. No.: WO94/21217

PCT Pub. Date: Sep. 29, 1994

[51] Int. Cl.$^6$ ............................................. A61K 7/06
[52] U.S. Cl. ..................... 514/564; 514/772; 514/943
[58] Field of Search ................................. 514/564

[56] References Cited

U.S. PATENT DOCUMENTS

| | | |
|---|---|---|
| 3,426,137 | 2/1969 | Philpitt . |
| 4,039,669 | 8/1977 | Beyler et al. . |
| 4,139,638 | 2/1979 | Neri et al. . |
| 4,161,540 | 7/1979 | Neri et al. . |
| 4,191,775 | 3/1980 | Glen . |
| 4,269,831 | 5/1981 | Ferrari et al. . |
| 4,344,941 | 8/1982 | Wiechert et al. . |
| 4,370,315 | 1/1983 | Greff et al. . |
| 4,439,432 | 3/1984 | Peat . |
| 4,508,714 | 4/1985 | Cecic et al. . |
| 4,517,175 | 5/1985 | Iwabuchi et al. . |
| 4,720,489 | 1/1988 | Shander . |
| 4,737,361 | 4/1988 | Rafft et al. ........................ 424/65 |
| 4,885,289 | 12/1989 | Breuer et al. . |
| 4,935,231 | 6/1990 | Pigiet . |
| 4,970,216 | 11/1990 | Deckner et al. ...................... 514/31 |
| 5,095,007 | 3/1992 | Ahluwalia . |
| 5,096,911 | 3/1992 | Ahluwalia et al. . |
| 5,132,293 | 7/1992 | Shander et al. . |
| 5,143,925 | 9/1992 | Shander et al. . |
| 5,189,212 | 2/1993 | Ruenitz . |
| 5,271,942 | 12/1993 | Heverhagen . |
| 5,300,284 | 4/1994 | Wiechers et al. . |
| 5,364,885 | 11/1994 | Ahluwalia et al. . |
| 5,411,991 | 5/1995 | Shander et al. . |
| 5,455,234 | 10/1995 | Ahluwalia et al. . |
| 5,468,476 | 11/1995 | Ahluwalia et al. . |
| 5,474,763 | 12/1995 | Shander et al. . |

FOREIGN PATENT DOCUMENTS

| | | |
|---|---|---|
| 0 413 528 A1 | 2/1991 | European Pat. Off. . |
| 0 532 219 A2 | 3/1993 | European Pat. Off. . |
| 1 458 349 | 12/1976 | United Kingdom . |
| 8602269 | 4/1986 | WIPO . |

OTHER PUBLICATIONS

Sato, "The Hair Cycle and Its Control Mechanism", *Biology and Disease of the Hair* pp. 3–13 (1975).
Goos et al., "An Improved Method for Evaluating Antiandrogens", *Arch. Dermatol. Res.*, 273:333–341 (1982).
Messenger, "The Control of Hair Growth: An Overview", *The Journal of Investigative Dermatology*, 101:4s–9s, supplement, (1993).
Simpson et al., "The Effect of Topically Applied Progesterone on Sebum Excretion Rate", *British Journal of Dermatology*, 100:687–692 (1979).
Harmon et al., "12–0–Tetradecanoylphorbol–13–Acetate Inhibits Human Hair Follicle Growth and Hair Fiber . . . ", *SID Abstracts*, 102:533 (1994).
"Cochlear damage and increased threshold in alphadifluoromethylorinthine (DFMO) treated guinea pigs" (abstract only) 1990.

*Primary Examiner*—Rebecca Cook
*Attorney, Agent, or Firm*—Fish & Richardson P.C.

[57] ABSTRACT

The present invention embraces a topical composition for inhibiting mammalian hair growth, particularly human beard hair growth (including hirsutism), comprising a water-soluble, hair-growth-inhibiting agent dispersed in an oil-in-water emulsion in the form of a lotion or cream. The invention also embraces a method of inhibiting mammalian hair growth by applying an effective amount of the above composition to the skin. The invention further embraces a topical composition for delivering a pharmacological agent to the skin.

11 Claims, No Drawings

TOPICAL COMPOSITION FOR INHIBITING HAIR GROWTH

This application is a 371 of PCT/US93/05068 filed May 27, 1993.

BACKGROUND OF THE INVENTION

This invention relates to a new topical composition for inhibiting mammalian hair growth. It also relates to a method of inhibiting hair growth by applying a topical composition according to this invention to the skin.

In U.S. Pat. No. 4,720,489 it is disclosed that the topical application of a composition comprising an ornithine decarboxylase ("ODC") inhibitor will inhibit hair growth, including beard hair growth. A particularly advantageous ODC inhibitor for use in this application is 2-(difluoromethyl)-2,5-diaminopentanoic acid, also identified as α-(difluoromethyl)ornithine ("DFMO"). This patent demonstrates the effectiveness of ODC inhibitors for inhibiting hair growth by measuring changes in flank organ hair mass in adult male hamsters treated with ethanol solutions of such compounds. The patent also generally proposes the possible incorporation of ODC inhibitors in cosmetic formulations such as skin lotions and creams, but the effectiveness of such proposed formulations and their stability and aesthetic attributes are unknown. Since DFMO is a highly ionic material, it would tend to destabilize emulsion systems and would be difficult to formulate in such systems, particularly at higher dosage levels necessary to achieve maximum efficacy.

In U.S. Pat. No. 5,095,007, U.S. Pat. No. 5,096,911, and U.S. Pat. No. 5,132,293, additional hair growth inhibitors are disclosed which are completely unrelated to the aforementioned ODC inhibitors. However, each of these patents discloses a water-ethanol vehicle for delivering the active compound. The vehicle comprises 68% water, 16% ethanol, 5% propylene glycol, 5% dipropylene glycol, 4% benzyl alcohol, and 2% propylene carbonate. This vehicle is not aesthetically pleasing or easy to use since it is very runny and feels wet and tacky. Moreover, the efficacy of the active material in this vehicle may not be optimum even though the vehicle contains two known penetration enhancers, namely benzyl alcohol and propylene carbonate.

It is an object of the present invention to provide a topical composition for inhibiting hair growth which is stable, highly efficacious and aesthetically pleasing.

SUMMARY OF THE INVENTION

The present invention embraces a topical composition for inhibiting mammalian hair growth, particularly human beard hair growth (including hirsutism), comprising a water-soluble, hair-growth-inhibiting agent dispersed in an oil-in-water emulsion in the form of a lotion or cream. The invention also embraces a method of inhibiting mammalian hair growth by applying an effective amount of the above composition to the skin. The invention further embraces a topical composition for delivering a water-soluble, pharmacological agent to the skin.

DETAILED DESCRIPTION OF THE INVENTION

The hair growth inhibiting agent which is utilized in the composition and method of the present invention may be any water-soluble, hair-growth-inhibiting agent, particularly any highly ionic, water-soluble, hair-growth-inhibiting agent. Such active agents may be selected from any of the classes of agents described in the aforementioned U.S. patents, namely U.S. Pat. No. 4,720,489, U.S. Pat. No. 5,095,007, U.S. Pat. No. 5,096,911, and U.S. Pat. No. 5,132,293, provided such agents are water soluble. In a preferred embodiment, the hair growth inhibiting agent is 2-(difluoromethyl)-2,5-diaminopentanoic acid, which is also identified as α-(difluoromethyl)ornithine, hereinafter abbreviated "DFMO".

The topical composition of the present invention comprises about 1 to 20 parts by weight, preferably 5 to 15 parts, of the aforedescribed water-soluble, hair-growth-inhibiting agent, particularly DFMO, dispersed in 99 to 80 parts by weight, preferably 95 to 85 parts, of a vehicle comprising an oil-in-water emulsion of the formula (the last two ingredients being optional):

| Ingredient | Wt. Percent | Ex. I | Ex. II |
| --- | --- | --- | --- |
| Water | 78 to 87 | 80.84* | 85.53* |
| Glyceryl Stearate[1] | 2.8 to 4.8 | 4.24 | 2.97 |
| PEG-100 Stearate[1] | 2.7 to 4.7 | 4.09 | 2.86 |
| Cetearyl Alcohol[2] | 1.9 to 3.3 | 3.05 | 2.14 |
| Ceteareth-20[2] | 1.6 to 2.7 | 2.50 | 1.75 |
| Mineral Oil | 1.7 to 2.7 | 2.22 | 2.22 |
| Stearyl Alcohol[3] | 1.0 to 2.0 | 1.67 | 1.17 |
| Dimethicone[4] | 0.3 to 1.0 | 0.56 | 0.56 |
| Citric Acid[5] | 0 to 0.5 | — | 0.25 |
| Sodium Hydroxide[6] | q.s. | q.s. | q.s. |

*0.5% water withheld for subsequent pH adjustment.
[1] Available as a blend, for example Cithrol GMS A/S ES0743 from Croda Chemicals Ltd. (U.K.).
[2] Available as a blend, for example Cosmowax EM5483 from Croda Chemicals Ltd. (U.K.).
[3] Available as Lorol-18 from Henkel Chemicals Ltd.
[4] Available as Silicone Fluid 200 - 100 cps from Dow Corning Corporation (e.g., 360 Medical Fluid or Q7-9120 Fluid).
[5] Other weak acids may be substituted, for example lactic, tartaric or phosphoric acids to serve as a pH buffer.
[6] Quantity sufficient to adjust pH to about 3.5. Other strong bases, such as KOH, may be used or, in some cases, strong acids such as HCl, where the pH needs to be lowered.

The active agent plus vehicle will total 100 parts by weight when finished. Minor amounts of other ingredients, such as dyes, fragrances, and biocidal agents or preservatives may be incorporated in the vehicle as deemed necessary or desirable. It is preferred to add about 0.5 to 0.9 parts of Phenonip, a biocidal agent available from Nipa Laboratories Ltd. (U.K.), to the above formulation.

The following procedure is carried out to make the vehicle utilized in the topical composition of the present invention. The water and water soluble components, are charged to a mixing vessel, the pH is adjusted to about 3.5, and the solution is heated to about 70° C. The oil soluble components, except for the biocidal agent, are melted together at about 70° C., then run into the water phase with brisk stirring. Mixing is continued for about twenty minutes, then water cooling is applied. The biocidal agent is added at 40°–45° C. and stirring is continued until the temperature reaches 25° C. to yield a white, soft cream with a viscosity of about 8,000–12,000 cps. If it is desired to increase the viscosity of the resulting emulsion, shear can be applied using a conventional homogenizer, for example a Silverson L4R homogenizer with a square hole high shear screen.

Normally, this step is not required since the viscosity of the emulsion can increase during dissolution of the active agent.

The topical composition of the present invention is made by blending about 1 to 20 parts by weight, preferably 5 to 15 parts, of the hair-growth-inhibiting active agent, preferably DFMO, with correspondingly 99 to 80 parts by weight, preferably 95 to 85 parts, of the vehicle prepared as described above, and adjusting the pH to about 3.5 with aqueous sodium hydroxide (10%) or hydrochloric acid (10%). Of course, the topical composition could also be fabricated by including the active agent in the water phase during the aforedescribed vehicle preparation.

EXAMPLE

Two vehicles were prepared having the composition designated Ex. I and Ex. II in the above Table according to the aforedescribed procedure. The two vehicles contained 0.83 and 0.55 parts Phenonip respectively. To four separate batches of each vehicle was then added with mixing sufficient DFMO to produce topical compositions containing 2.5, 5, 10 and 15% DFMO. Thus, a total of eight topical compositions were prepared in all. Each composition was tested for hair growth inhibition using a standard hamster flank organ hair mass study as described in the previously identified four U.S. patents. For comparison, a control composition containing vehicle only was tested (I-V and II-V below), as well as a composition containing 10% DFMO in the water-ethanol vehicle shown in Ex. I of U.S. Pat. No. 5,096,911 (W-E below). The results of these studies were as follows:

| Composition | % Inhibition | Composition | % Inhibition |
|---|---|---|---|
| I-A (15% DFMO) | 84.2 | II-A (15% DFMO) | 89.1 |
| I-B (10% DFMO) | 87.6 | II-B (10% DFMO) | 91.4 |
| I-C (5% DFMO) | 84.5 | II-C (5% DFMO) | 85.5 |
| I-D (2.5% DFMO) | 60.0 | II-D (2.5% DFMO) | 81.4 |
| I-V (0% DFMO) | — | II-V (0% DFMO) | — |
| W-E (10% DFMO) | 68.3 | W-E (10% DFMO) | 72.6 |

As can be seen, each of the compositions of the invention, namely I-A through I-D and II-A through II-D, were highly efficacious in inhibiting mammalian hair growth. Similarly, beard hair growth inhibition is obtained when such compositions are applied to the human face. Remarkably, the above data also demonstrate that the present compositions are superior in efficacy to a water-ethanol composition which contains penetration enhancers. This suggests that the present composition achieves either enhanced skin penetration of the active agent or increased residence time of the active agent at the treated site. Moreover, the compositions of the invention remain stable over an extended period of time and have aesthetically pleasing attributes.

The topical compositions of the present invention are applied to mammalian skin, particularly the human face, on a daily or twice daily basis to provide a level of active agent of about 10 to 2000 micrograms per square centimeter of skin. Obviously, the application dose may be varied to achieve a suitable level of effectiveness for each individual being treated.

It will be apparent that equivalent materials may be substituted for those specified in the aforementioned table of ingredients without departing from the spirit and scope of this invention. For example, other water-soluble, pharmacological agents may be delivered to the skin by incorporating from about 1 to 20% of such an agent in the previously described vehicle.

We claim:

1. A topical composition for inhibiting mammalian hair growth which comprises about 1 to 20 parts by weight of a water-soluble, hair-growth-inhibiting active agent dispersed in about 99 to 80 parts by weight correspondingly of a vehicle comprising an oil-in-water emulsion of the following components in parts by weight:

| Water | 78 to 87 |
|---|---|
| Glyceryl Stearate | 2.8 to 4.8 |
| PEG-100 Stearate | 2.7 to 4.7 |
| Cetearyl Alcohol | 1.9 to 3.3 |
| Ceteareth-20 | 1.6 to 2.7 |
| Mineral Oil | 1.7 to 2.7 |
| Stearyl Alcohol | 1.0 to 2.0 |
| Dimethicone | 0.3 to 1.0 |

2. The composition of claim 1, adjusted to a pH of about 3.5 and optionally comprising a pH buffer.

3. The composition of claim 1, comprising 5 to 15 parts by weight of said active agent dispersed in 95 to 85 parts by weight correspondingly of said vehicle.

4. The composition of claim 3, wherein said vehicle comprises an oil-in-water emulsion of the following components in parts by weight:

| Water | 80.84 |
|---|---|
| Glyceryl Stearate | 4.24 |
| PEG-100 Stearate | 4.09 |
| Cetearyl Alcohol | 3.05 |
| Ceteareth-20 | 2.50 |
| Mineral Oil | 2.22 |
| Stearyl Alcohol | 1.67 |
| Dimethicone | 0.56 |

5. The composition of claim 3, wherein said vehicle comprises an oil-in-water emulsion of the following components in parts by weight:

| Water | 85.53 |
|---|---|
| Glyceryl Stearate | 2.97 |
| PEG-100 Stearate | 2.86 |
| Cetearyl Alcohol | 2.14 |
| Ceteareth-20 | 1.75 |
| Mineral Oil | 2.22 |
| Stearyl Alcohol | 1.17 |
| Dimethicone | 0.56 |
| Citric Acid | 0.25 |

6. The composition of claim 1, 2, 3, 4, or 5, wherein said active agent is 2-(difluoromethyl)-2,5-diaminopentanoic acid.

7. A method of inhibiting mammalian hair growth which comprises applying to the skin of a mammal an effective amount of a topical composition according to claim 1, 2, 3, 4, or 5.

8. The method of claim 7, wherein the active agent in said topical composition is 2-(difluoromethyl)-2,5-diaminopentanoic acid.

9. The method of claim 8, wherein said topical composition is applied daily or twice daily at a level sufficient to provide about 10 to about 2000 micrograms of active agent per square centimeter of skin.

10. The method of claim 8, wherein said topical composition is applied to human skin.

11. A topical composition for delivering a water-soluble, pharmacological agent to the skin which comprises about 1 to 20 parts by weight of said water-soluble, pharmacological agent dispersed in about 99 to 80 parts by weight correspondingly of a vehicle comprising an oil-in-water emulsion of the following components in parts by weight:

| | |
|---|---|
| Water | 78 to 87 |
| Glyceryl Stearate | 2.8 to 4.8 |
| PEG-100 Stearate | 2.7 to 4.7 |
| Cetearyl Alcohol | 1.9 to 3.3 |
| Ceteareth-20 | 1.6 to 2.7 |
| Mineral Oil | 1.7 to 2.7 |
| Stearyl Alcohol | 1.0 to 2.0 |
| Dimethicone | 0.3 to 1.0 |

\* \* \* \* \*